United States Patent
DiMartino

(10) Patent No.: US 6,905,669 B2
(45) Date of Patent: Jun. 14, 2005

(54) COMPOSITIONS AND METHODS FOR REESTABLISHING GENE TRANSCRIPTION THROUGH INHIBITION OF DNA METHYLATION AND HISTONE DEACETYLASE

(75) Inventor: Jorge F. DiMartino, San Carlos, CA (US)

(73) Assignee: SuperGen, Inc., Dublin, CA (US)

(*) Notice: Subject to any disclaimer, the term of this patent is extended or adjusted under 35 U.S.C. 154(b) by 0 days.

(21) Appl. No.: 09/841,744

(22) Filed: Apr. 24, 2001

(65) Prior Publication Data

US 2004/0204339 A1 Oct. 14, 2004

(51) Int. Cl.[7] .................... A61K 49/00; C07H 19/06
(52) U.S. Cl. ............... 424/9.1; 536/28.5; 536/28.51; 536/28.52; 549/511; 546/113; 514/9; 514/11; 514/449; 514/459; 514/460
(58) Field of Search .................... 536/28.5, 28.51, 536/28.52; 549/511; 546/113; 514/9, 11, 449, 459, 460, 49; 424/9.1; 414/9.1

(56) References Cited

U.S. PATENT DOCUMENTS

| | | | | |
|---|---|---|---|---|
| 5,283,383 A | * | 2/1994 | Boyd et al. | 570/189 |
| 6,110,697 A | | 8/2000 | Dulski et al. | 435/18 |
| 2002/0114809 A1 | * | 8/2002 | Rubinfeld et al. | 424/155.1 |

FOREIGN PATENT DOCUMENTS

| | | | |
|---|---|---|---|
| WO | WO 98/55449 | * | 12/1998 |
| WO | WO 02/069903 A2 | | 9/2002 |
| WO | WO 02/069903 | | 9/2002 |

OTHER PUBLICATIONS

Zhu et al., DNA Methyltransferase Inhibition Enhances Apoptosis Induced by Histone Deacetylase Inhibitors. Cancer Research 61, 1327–1333 (Feb. 15, 2001).*
Saito et al., A Synthetic inhibitor of Histone Deacetylase, MS–27–275, with Marked in vivo Antitumor activity against Human Tumors. Proc. Natl.Acad. Sci. USA 96, 4592–4597 (Apr. 1999).*
Zhu et al., A nonsteriodal anti–inflammatory drug, flufenamic acid, inhibits the expression of the androgen receptor in LNCap cells. Endocrinology 140, 5451–5454 (Nov. 1999).*
Yoshida et al., J. Biol. Chem. 265, 17174–17179 (1990).*
Guan et al. Drg–1 as differentiation–related putative metastatic suppressor gene in human colon cancer. Cancer Research 60, 749–755 (Feb. 2000).*
Nakayama et al., Epigenetic regulation of androgen receptor gene expression in human prostate cancers. Lab. Invest. 80, 1789–1796 (Dec. 2000).*
Kijima et al., Trtapoxin, an antitumor cyclic tetrapeptide, is an irreversible inhibitor of mammalian histone deacetylase. J. Biol. Chem. 268, 22429–22435 (1993).*

Cameron et al. Synergy of demethylation and histone deacetlase inhibition in the re–expression of genes silenced in cancer. Nature Genetics 21, 103–107 (Jan. 1999).*
Sheikhnejad, G. et al., "Mechanism of inhibition of DNA (cytosine C5)– methyltransferases by oligodeoxyribonucleotides containing 5, 6–dihydro–5–azacytosine", *J. Mol. Biol.*, 1999, pp. 2021–2034, vol. 285.
Goffin, J. et al., "DNA methyltransferase inhibitors—state of the art", *Annals of Oncology*, 2002, pp. 1699–1716, vol. 13.
Wijermans, P. et al., "Low–dose 5–aza–2'–deoxycytidine, a DNA hypomethylating agent, for the treatment of high–risk myelodysplastic syndrome: a multicenter phase II study in elderly patients", *Journal of Clinical Oncology*, Mar. 2000, pp. 956–962, vol. 18, No. 5.
Goffin, J., et al., "DNA Methyltransferase Inihibitors–State of the Art, "*Annals of Oncology*(2002) vol. 13, pp. 1699–1716.
Sheikhnejad, G., et al., "Mechanism of Inhibition of DNA (Cytosine C5)– Methyltransferases by Oligodeoxyribonucleotides Containing 5, 6–Dihydro–5– Azacytosine," *J. Mol. Biol.* (1999) vol. 285, pp. 2021–2034.
Wijermans, P., et al., "Low–Dose 5–Aza–2'–Deoxycytidine, a DNA Hypomethylating Agent, for The Treatment of High–Risk Mylodyplastic Snydrome: A Multicenter Phase II Study in Elderly Patients," *Journal of Clinical Oncology* (2000) vol. 18, No. 5, pp. 956–962.
Baylin, S.B., et al., "Alterations in DNA Methylation: A Fundamental Aspect of Neoplasia," *Cancer Res.*, (1998) 72:141–196.
Daskalakis,M., et al., "Expression of a Hypermethylated and Silenced P15/INK4B Gene in a Subgroup of MDS Patients is Restored by Treatment With The Methylation Inhibitor 5–AZA–2'–Deoxycytidine," *Abstracts Leukemia Research* (2001) Suppl. No. 1, S16–S17.
Esteller, M., "A Gene Hypermethylation Profile of Human Cancer," *Cancer Research* (2001) 61:3225–3229.
Esteller, M., "CpG Island Hypermethylation and Tumor Suppressor Genes: a Booming Present, a Brighter Future," *Oncogene* (2002) 21:5427–5440.

(Continued)

*Primary Examiner*—Jon Weber
*Assistant Examiner*—Chih–Min Kam

(57) ABSTRACT

Compositions and methods are provided for treating diseases associated with aberrant silencing of gene expression such as cancer by reestablishing the gene expression through inhibition of DNA hypomethylation and histone deacetylase. The method comprises: administering to a patient suffering from the disease a therapeutically effective amount of a DNA methylation inhibitor such as a cysteine analog such as decitabine, in combination with an effective amount of histone deacetylase inhibitor such as hydroxamic acid, cyclic peptide, benzamide, butyrate, and depudecin.

18 Claims, 3 Drawing Sheets

OTHER PUBLICATIONS

Esteller, M., "Epigenetic Lesions Causing Genetic Lesions in Human Cancer: Promoter Hypermethylation of DNA Repair Genes," *European Journal of Cancer* (2000) 36:2294–2300.

Gagnon, J., et al., "Interaction of 5–aza–2'–deoxycytidine and Depsipeptide on Antineoplastic Activity and Activation of 14–3–3σ, E–Cadherin And Tissue Inhibitor of Metalloproteinase 3 Expression in Human Breast Carcinoma Cells," *Anti–Cancer Drugs,* (2003), 14(3):193–202.

Jones, P.A., "DNA Methylation And Cancer," *Oncogene,* (2002) 21:5358–5360.

Jones, P.A., et al., "The Fundamental Role of Epigenetic Events in Cancer," *Nature Reviews/Genetics,* (2002) 3:415–428.

Jones, P.A., et al., "The Role of DNA Methylation in Cancer," *Adv. Cancer Res.,* (1990) 54:1–23.

Karpf, A.R., et al., "Reactivating The Expression of Methylation Silenced Genes in Human Cancer," *Oncogene,* (2002) 21:5496–5503.

La Rosee, P., et al., "In Vitro Efficacy of Combined Treatment Depends on the Underlying Mechanism of Resistance in Imatinib–Resistant Bcr–Abl positive Cell Lines," *Blood First Edition Paper,* prepublished online (2003) DOI 10.1182/blood–2003–04–1074, pp. 1–39.

Nephew, K.P., et al., "Epigenetic Gene Silencing in Cancer Initiation And Progression," *Cancer Letters 190,* (2003) pp. 125–133.

Paz, M.F., et al., "A Systematic Profile of DNA Methylation in Human Cancer Cell Lines," *Cancer Research 63,* (2003) 1114–1121.

Primeau, M., et al., "Synergistic Antineoplastic Action of DNA Methylation Inhibitor 5– AZA–2'–Deoxycytidine and Histone Deacetylase Inhibitor Depsipeptide on Human Breast Carcinoma Cells," *Int. J. Cancer,* (2003) 103:177–184.

Santini, V., et al., "Changes in DNA Methylation in Neoplasia: Pathophysiology and Therapeutic Implications," *Annals of Internal Medicine* (2001) 134:573–586.

Schrump, D.S., et al., "Phase 1 Study of Sequential Deoxyazacytidine/Depsipeptide Infusion in Patients With Malignancies Involving Lungs or Pleura," *Clinical Lung Cancer,* (2002) 186–192.

Shaker, S., et al., "Preclinical Evaluation of Antineoplastic Activity of Inhibitors of DNA Methylation (5–aza–2'–deoxycytidine) and Histone Deacetylation (Trichostatin A, Depsipeptide) in Combination Against Myeloid Leukemic Cells," *Leukemia Research 27,* (2003) 437–444.

Smiraglia, D.J., et al., "The Study of Aberrant Methylation in Cancer *via* Restriction Landmark Genomic Scanning," *Oncogene,* (2002) 21:5414–5426.

Wajed, S.A., et al., "DNA Methylation: An Alternative Pathway to Cancer," *Annals of Surgery* (2001), 234(1):10–20.

Weiser, T.S., "Sequential 5–Aza–2'–Deoxycytidine–Depsipeptide FR901228 Treatment Induces Apoptosis Preferentially in Cancer Cells And Facilities Their Recognition by Cytolytic T Lymphocytes Specific for NY–ESO–1," *Journal of Immunotherapy,* (2001), 24(2):151–161.

Minoru Yoshida et al., "Potent and Specific Inhibition of Mammalian Histone Deacetylase Both in Vivo and in Vitro by Trichostatin A" J. Biol. Chem Oct. 15, 1990, vol. 265, No. 28, pp. 17174–17179.

Villanueva et al., "Induction of HTLV–1 Tax and Immune Genes in Infected Cells by Histone Deacetylase Inhibition and DNA Demethylation Agents", FASEB Journal, Mar. 2001, vol 15, No. 5, p. A1230, See Abstract B–631A.

Lan Yan et al., "Role of DNA Methylation and Histone Acetylation in Steriod Receptor Expression in Breast Cancer[1,4]," J. Mammary Gland Biology and Neoplasia, Apr. 2001, vol. 6, No. 2, pp. 183–192. See p. 189.

Coffee, et al., "Acetylated histones are associated with FMR1 in normal but not fragile X–syndrome cells", Nature Genetics, vol. 22, pp. 98–101 (1999).

Endres, et al., "DNA Methyltransferase Contributes to Delayed Ischemic Brain Injury", The Journal of Neuroscience, 20(9):3175–3181 (2000).

Koshy, et al., "2–deoxy 5–azacytidine and fetal hemoglobin induction in sickle cell anemia", Clinical Observations, Interventions, and Therapeutic Trials, Blood, vol. 96, No. 7, pp. 2379–2384 (2000).

Marks, et al., "Histone Deacetylase Inhibitors: Inducers of Differentiation of Apoptosis of Transformed Cells", Journal of the National Cancer Institute, vol. 92, No. 15, (2000).

* cited by examiner

5-azacytidine

5-aza-2'-deoxycytidine

I. Hydroxamic Acids

Trichostatin A (TSA)

Oxamflatin

Suberoylanilide Hydroxamic Acid (SAHA)

Suberic Bishydroxamic Acid (SBHA)

m-Carboxy-cinnamic acid
bishydroxamic Acid (CBHA)

Pyroxamide

FIGURE 2-cont.
II. Cyclic Peptides
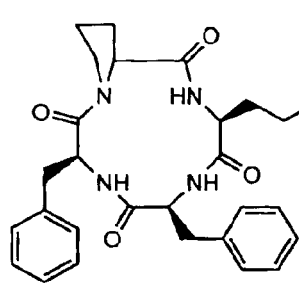
Trapoxin
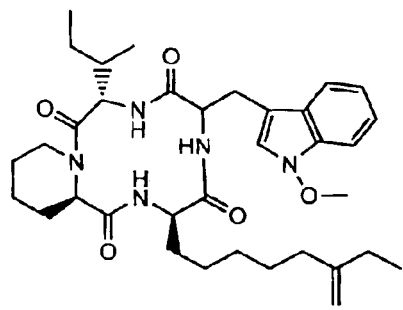
Apicidin
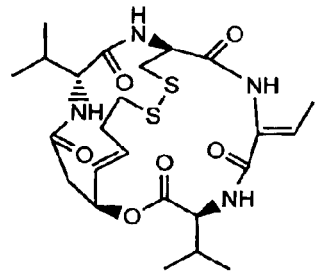
Depsipeptide
III. Butyamides
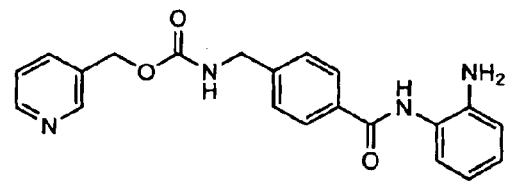
MS-27-275
IV. Butyrates
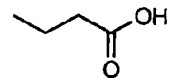
Butyric Acid
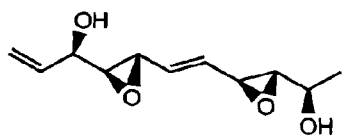
Depudecin

COMPOSITIONS AND METHODS FOR REESTABLISHING GENE TRANSCRIPTION THROUGH INHIBITION OF DNA METHYLATION AND HISTONE DEACETYLASE

BACKGROUND OF THE INVENTION

1. Field of the Invention

This invention relates to compositions and methods for using antineoplastic agents to treat diseases such as cancer, and more specifically, to compositions and methods for effectively treating these diseases through reestablishment of gene transcription with a combination therapy including a DNA methylation inhibitor and a histone deacetylase inhibitor.

2. Description of Related Art

The evolution of new therapies for diseases associated with abnormal cell proliferation such as cancer has provided many choices of therapeutics for clinical treatment. Recent development and FDA approval of biologic therapy for refractory tumors, such as melanoma, raises a new hope that more advances tumors that have been refractory to all approaches with conventional drugs may be curable by taking non-conventional approaches.

Currently therapeutic agents used in clinical cancer therapy are categorized into six groups: alkylating agents, antibiotic agents, antimetabolic agents, biologic agents, hormonal agents, and plant-derived agents.

The alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. The alkylating agents are cell cycle phase-nonspecific agents because they exert their activity independently of the specific phase of the cell cycle. The nitrogen mustards and alkyl alkone sulfonates are most effective against cells in the $G_1$ or M phase. Nitrosoureas, nitrogen mustards, and aziridines impair progression from the $G_1$ and S phases to the M phases. Chabner and Collins eds. (1990) "Cancer Chemotherapy: Principles and Practice", Philadelphia: J B Lippincott.

The alkylating agents are active against wide variety of neoplastic diseases, with significant activity in the treatment of leukemias and lymphomas as well as solid tumors. Clinically this group of drugs is routinely used in the treatment of acute and chronic leukemias; Hodgkin's disease; non-Hodgkin's lymphoma; multiple myeloma; primary brain tumors; carcinomas of the breast, ovaries, testes, lungs, bladder, cervix, head and neck, and malignant melanoma. The major toxicity common to all of the alkylating agents is myelosuppression. Gastrointestinal adverse effects of variable severity occur commonly and various organ toxicities are associated with specific compounds. Black and Livingston (1990) Drugs 39:489–501; and 39:652–673.

The antibiotic agents are a group of drugs that produced in a manner similar to antibiotics as a modification of natural products. Examples of antibiotic agents include anthracyclines (e.g. doxorubicin, daunorubicin, epirubicin, idarubicin and anthracenedione), mitomycin C, bleomycin, dactinomycin, plicatomycin. These antibiotic agents interferes with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death.

The antibiotic agents have been used as therapeutics across a range of neoplastic diseases, including carcinomas of the breast, lung, stomach and thyroids, lymphomas, myelogenous leukemias, myelomas, and sarcomas. The primary toxicity of the anthracyclines within this group is myelosuppression, especially granulocytopenia. Mucositis often accompanies the granulocytopenia and the severity correlates with the degree of myelosuppression. There is also significant cardia toxicity associated with high dosage administration of the anthracyclines.

The antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine.

Antimetabolic agents have widely used to treat several common forms of cancer including carcinomas of colon, rectum, breast, liver, stomach and pancreas, malignant melanoma, acute and chronic leukemia and hair cell leukemia. Many of the adverse effects of atnimetabolite treatment result from suppression of cellular proliferation in mitotically active tissues, such as the bone marrow or gastrointestinal mucosa. Patients treated with these agents commonly experience bone marrow suppression, stomatitis, diarrhea, and hair loss. Chen and Grem (1992) Curr. Opin. Oncol. 4:1089–1098.

The hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Hormonal agents are used to treat breast cancer, prostate cancer, melanoma and meningioma. Because the major action of hormones is mediated through steroid receptors, 60% receptor-positive breast cancer responded to first-line hormonal therapy; and less than 10% of receptor-negative tumors responded. The main side effect associated with hormonal agents is flare. The frequent manifestations are an abrupt increase of bony pain, erythema around skin lesions, and induced hypercalcemia.

Plant-derived agents are a group of drugs that are derived from plants or modified based on the molecular structure of the agents. Examples of plant-derived agents include vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission.

Plant-derived agents are used to treat many forms of cancer. For example, incristine is used in the treatment of the leukemias, Hodgkin's and non-Hodgkin's lymphoma, and the childhood tumors neuroblastoma, rhabdomyosarcoma, and Wilms' tumor. Vinblastine is used against the lymphomas, testicular cancer, renal cell carcinoma, mycosis fungoides, and Koposi's sarcoma. Doxetaxel has shown promising activity against advanced breast cancer, non-small cell lung cancer (NSCLC), and ovarian cancer. Etoposide is active against a wide range of neoplasms, of which small cell lung cancer, testicular cancer, and NSCLC are most responsive.

The plant-derived agents cause significant side effects on patients being treated. The vinca alkaloids display different spectrum of clinical toxicity. Side effects of vinca alkaloids include neurotoxicity, altered platelet function, myelosuppression, and leukopenia. Paclitaxel causes dose-limiting neutropenia with relative sparing of the other hematopoietic cell lines. The major toxicity of the epipophyllotoxins is hematologic (neutropenia and thrombocytopenia). Other side effects include transient hepatic enzyme abnormalities, alopenia, allergic reactions, and peripheral neuropathy.

Biologic agents are a group of biomolecules that elicit cancer/tumor regression when used alone or in combination with chemotherapy and/or radiotherapy. Examples of biologic agents include immuno-modulating proteins such as cytokines, monoclonal antibodies against tumor antigens, tumor suppressor genes, and cancer vaccines.

Cytokines possess profound immunomodulatory activity. Some cytokines such as interleukin-2 (IL-2, aldesleukin) and interferon-α (IFN-α) demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself.

Interferon-α includes more than 23 related subtypes with overlapping activities. IFN-α has demonstrated activity against many solid and hematologic malignancies, the later appearing to be particularly sensitive. Examples of interferons include, interferon-α, interferon-β (fibroblast interferon) and interferon-γ (fibroblast interferon). Examples of other cytokines include erythropoietin (epoietin-α), granulocyte-CSF (filgrastin), and granulocyte, macrophage-CSF (sargramostim). Other immuno-modulating agents other than cytokines include bacillus Calmette-Guerin, levamisole, and octreotide, a long-acting octapeptide that mimics the effects of the naturally occuring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein.

Another example of monoclonal antibodies against tumor antigens is RITUXAN® (Rituximab) that is raised against CD20 on lymphoma cells and selectively deplete normal and malignant CD20$^+$ pre-B and mature B cells. RITUXAN® is used as single agent for the treatment of patients with relapsed or refractory low-grade or follicular, CD20+, B cell non-Hodgkin's lymphoma.

MYELOTARG® and CAMPATH® are further examples of monoclonal antibodies against tumor antigens that may be used.

Tumor suppressor genes are genes that function to inhibit the cell growth and division cycles, thus preventing the development of neoplasia. Mutions in tumor suppressor genes cause the cell to ignore one or more of the components of the network of inhibitory signals, overcoming the cell cycle check points and resulting in a higher rate of controlled cell growth—cancer. Examples of the tumor suppressor genes include DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Examples of TAAs include gangliosides (GM2), prostate specific antigen (PSA), α-fetoprotein (AFP), carcinoembryonic antigen (CEA) (produced by colon cancers and other adenocarcinomas, e.g. breast, lung, gastric, and pancreas cancer), melanoma associated antigens (MART-1, gp100, MAGE 1,3 tyrosinase), papillomavirus E6 and E7 fragments, whole cells or portions/lysates of antologous tumor cells and allogeneic tumor cells.

Although thousands of potential anticancer agents have been evaluated, the treatment of human cancer remains fraught with complications and side effects which often present an array of suboptimal treatment choices. Despite the great number of anti-neoplastic agents that are used in the clinic for cancer treatment, a need still exists for more effective drug regimens for treating cancer in a more genetically specific manner. The present invention relates to one such improved drug regimen for treating diseases that can be controlled by manipulation of gene expression, such as cancer.

SUMMARY OF THE INVENTION

The present invention provides new and improved compositions, kits, and methods for treating diseases such as cancer using a combination therapy which includes a DNA methylation inhibitor and a histone deactylase inhibitor. The combination therapy triggers cancer cell death through reestablishment of the intrinsic death mechanisms of cells such as growth arrest, differentiation and apoptosis through activation of genes selectively silenced in cancer cells. The cancer cells sensitized by such a combination die quickly or become more prone to cell death signals sent by administration of conventional anti-neoplastic agents. Through such a genetic manipulation of the cancer cells, a lower dosage of the inhibitors and/or the anti-neoplastic agents may be required for achieving a superior clinical outcome to that using a conventional cancer therapy.

In one embodiment, the DNA methylation inhibitor is a cytidine analog or derivative. Examples of the cytidine analog or derivative include but art not limited to 5-azacytidine and 5-aza-2'-deoxycytidine. In a preferred variation of this embodiment, the DNA methylation inhibitor is 5-aza-2'-deoxycytidine (5-aza-CdR or decitabine).

According to this embodiment, the histone deacetylase inhibitor is selected from the group consisting of hydroxamic acids, cyclic peptides, benzamides, short-chain fatty acids, and depudecin.

Examples of hydroxamic acids and hydroxamic acid derivatives include, but are not limited to, trichostatin A (TSA), suberoylanlide hydroxamic acid (SAHA), oxamflatin, suberic bishydroxamic acid (SBHA), m-carboxy-cinnamic acid bishydroxamic acid (CBHA), and pyroxamide. Examples of cyclic peptides include, but are not limited to, trapoxin A apicidin and FR901228. Examples of benzamides include but are not limited to MS-27-275 (N-(2-aminophenyl)-4-[N-(pyridin-3-ylmethoxycarbonyl) aminomethyl]benzamide). Examples of short-chain fatty acids include but are not limited to butyrates (e.g., butyric acid and phenylbutyrate (PB)).

The compositions, kits and methods of the present invention may be used to treat a wide variety of indications such as hematological disorders and cancer.

Hematologic disorders include abnormal growth of blood cells which can lead to dysplastic changes in blood cells and hematological malignancies such as various leukemias. Examples of hematological disorders include but are not limited to acute myeloid leukemia, acute promyelocytic leukemia, acute lymphoblastic leukemia, chronic myelogenous leukemia, the myelodysplastic syndromes, and sickle cell anemia.

Examples of cancers include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

In regard to the kits of the present invention, the kits may comprise a DNA methylation inhibitor such as decitabine in combination with one or more histone deacetylase inhitors. In one particular embodiment, the DNA methylation inhibitor is decitabine and the histone deacetylase inhibitor is depsipeptide.

In regard to the methods of the present invention, the method may comprise administering to a patient suffering from a disease associated with aberrant silencing of gene expression a therapeutically effective amount of a DNA methylation inhibitor such as decitabine, and a histone deacetylase inhibitor. The DNA methylation inhibitor and the histone deacetylase inhibitor may be delivered separately or in combination. In a preferred embodiment, the DNA methylation inhibitor is administered prior to administering the histone deacetylase inhibitor.

The DNA methylation inhibitor and the anti-neoplastic agent may be delivered via various routes of administration. They may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms. In a preferred embodiment, the DNA methylation inhibitor is administered intravenously or subcutaneously, and the histone deacetylase inhibitor is administered intravenously.

The inventive combination of therapeutic agents and/or compositions may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

In a preferred embodiment, decitabine is administered into the patient via an 1–24 hour i.v. infusion per day for 3–5 days per treatment cycle at a dose preferably ranging from 1–100 mg/m$^2$, more preferably ranging from 2–50 mg/m$^2$, and most preferably from 5–20 mg/m$^2$. The preferred dosage below 50 mg/m$^2$ for decitabine is considered to be much lower than that used in conventional chemotherapy for cancer.

In another embodiment, the histone deacetylase inhibitor is depsipeptide. According to this embodiment, depsipeptide is administered to a patient by continuous i.v. infusion for at least 4 hours per day for a week at a dose preferably ranging from 2–100 mg/m$^2$, more preferably ranging from 5–50 mg/m$^2$, and most preferably from 5–15 mg/m$^2$. The treatment cycle may be 1 or 2 weeks per month.

The formulation for the continuous i.v. infusion of depsipeptide may be formed by resuspending up to 5 mg/ml of depsipeptide in an ethanol based. The suspension is then further diluted in normal saline for iv administration.

In yet another embodiment, the histone deacetylase inhibitor is phenylbutyrate (PB). According to this embodiment, PB is administered to a patient by continuous i.v. infusion for 2 to 3 weeks at a dose preferably ranging from 100–2000 mg/m$^2$, more preferably ranging from 250–1000 mg/m$^2$, and most preferably from 500–800 mg/m$^2$.

Also according to the present invention, after the treatment with the DNA methylation inhibitor and histone deacetylase inhibitor, the patient may be further treated with various anticancer agents such as alkylating agent, antibiotic agent, retinoid, antimetabolic agent, hormonal agent, plant-derived agent, anti-angiogenesis agent and biologic agent. Owing to the sensitizing effects of the combination therapy on the cells to apoptosis, the dosage of anticancer agents used for the treatment may be lower than that used in a convention cancer treatment regimen. Thus, a better clinical outcome may be achieved by using the compositions and methods of the present invention.

DETAILED DESCRIPTION OF THE INVENTION

Figure 1:
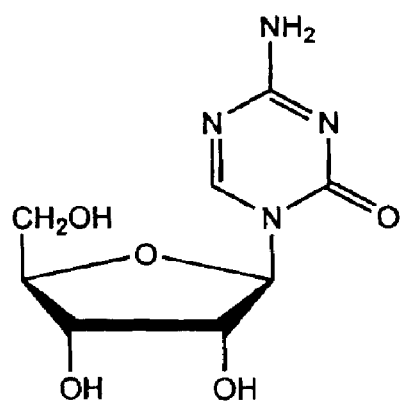
FIG. 1 illustrates chemical structures for 5-azacytidine and 5-aza-2'-deoxycytidine.
Figure 1:
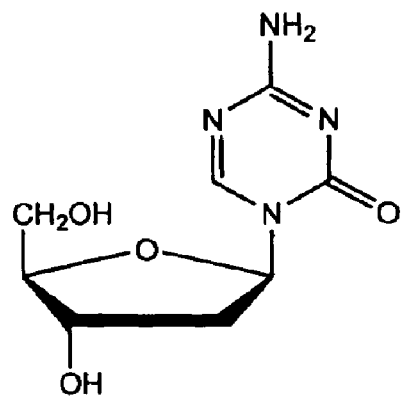

The present invention provides new and improved compositions, kits, and methods for treating diseases such as cancers using a combination therapy which includes a DNA methylation inhibitor, and a histone deacetylase inhibitor. By administering such a combination therapy to a host whose genes related to the disease have been transcriptionally silenced by aberrant methylation and histone deacetylase, activation of the genes have reestablished by inhibition of this aberrant biochemical modification of the genes.

According to the present invention, aberrant transcriptional silencing of a number of genes, such as tumor suppressor genes, is directly related to pathogenesis of cancer and other diseases. Methylation of cytosine residues in DNA and removal of acetyl groups from histones are the two primary mechanisms for gene silencing. Due to methylation and/or histone deacetylase of cancer-related genes, expression of these genes is suppressed or completely silenced. Meanwhile, expression of these genes is required for induction of growth arrest, differentiation, and/or apoptotic cell death of transformed cells. Inaction of these genes in the transformed cells leads to uncontrolled proliferation of these cells, which eventually results in cancer.

The present invention offers an effective method for reactivating the genes required for induction of growth arrest, differentiation and cell death of transformed cells. According to the present invention, a DNA methylation inhibitor inhibits methylation of DNA for the genes, especially in the regulatory region, thus resulting in activation of transcription of the gene. DNA methylation inhibitor is preferably a DNA methyltransferase inhibitor.

Meanwhile, a histone deacetylase inhibitor inhibits deacetylase of the histones in the nucleosomal core of the gene, thus resulting in net increase of the acetylation of histones, which, in turn, activates transcription of the gene. By exploiting these two complementary mechanisms, the combination therapy of the present invention may reestablish gene transcription more effectively and, ideally, in a synergistic manner. A combination therapy having synergistic effects should require a less amount of each inhibitor than it being used alone, thus reducing potential side effects associated systemic administration of high dosages of the inhibitors.

Further, since the combination therapy triggers cancer cell death through reestablishment of the intrinsic death mechanisms in cancer cells, the cancer cells sensitized by such an action die quickly or become more prone to cell death signals sent by administration of conventional anti-neoplastic agents. The combined inhibition of both DNA methylation and histone deacetylase effectively alters the fate of the cancer cells at a genetic level from uncontrolled proliferation to growth arrest, differentiation and apoptosis through activation of the genes selectively silenced in the cancer cells. Through such a synergistic genetic manipulation of the cancer cells, a lower dosage of the inhibitors may be required for treating both naive and metastatic cancers. In particular, metastatic cancer may be treated more efficaciously by reactivating those genes that are important components of apoptosis machinery (e.g. caspases) but are selectively repressed by the metastatic cancer cells to gain growth advantages. Reestablishment of expression of these apoptosis genes by using the combination therapy of the present invention should induce death of the metastatic cancer cells and therefore achieve a superior clinical outcome to that using a conventional cancer therapy.

Moreover, the method of the present invention offers a novel approach to improve therapeutic index of an anticancer agent used in combination with the two inhibitors. Many anticancer agents exert their anti-cancer effects by triggering signal transduction cascades involving proteins encoded by these tumor suppressor genes. With insufficient expression of these genes in cancer cells, the anti-cancer effects of these anti-neoplastic agents may be severely reduced or completely eradicated. Through reactivation or re-expression of these genes that are epigenetically silenced by DNA methylation and histone deacetylase, the intrinsic defense mechanisms of the body are mobilized to combat the disease by restoration of the tumor-suppressing functions to cancer cells in response to signals sent by the anti-cancer agent administered. Such stimulation of the intrinsic tumor suppressing functions of the body should lead to the requirement of lower dosage of the anticancer agent, thus resulting in a higher therapeutic index (i.e., greater efficacy and lower toxicity) of the agent.

In one embodiment, the DNA methylation inhibitor is a cytidine analog or derivative. Examples of the cytidine analog or derivative include but art not limited to 5-azacytidine and 5-aza-2'-deoxycytidine. In a preferred variation of this embodiment, the DNA methylation inhibitor is 5-aza-2'-deoxycytidine (5-aza-CdR or decitabine). Chemical structures for 5-azacytidine and 5-aza-2'-deoxycytidine are shown in FIG. 1.

According to this embodiment, the histone deacetylase inhibitor is selected from the group consisting hydroxamic acids, cyclic peptides, benzamides, short-chain fatty acids, and depudecin.

Figure 2:
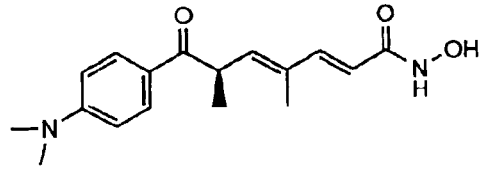
FIG. 2 illustrates chemical structures for some of these histone deacetylase inhibitors.
Figure 2:
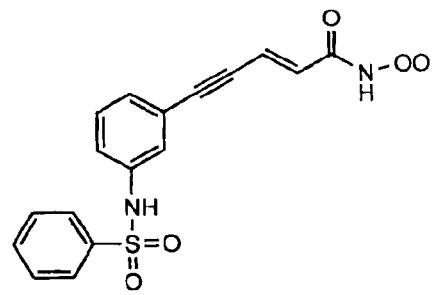
Figure 2:
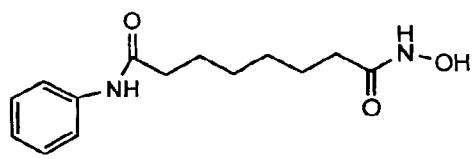
Figure 2:
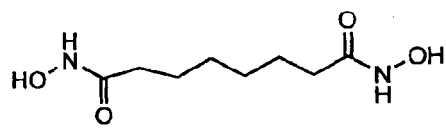
Figure 2:
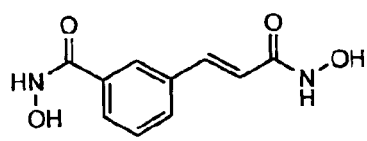
Figure 2:
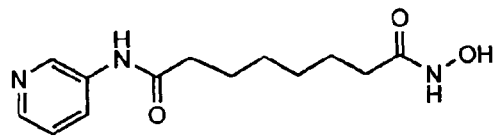

Examples of hydroxamic acids and hydroxamic acid derivatives include, but are not limited to, trichostatin A (TSA), suberoylanilide hydroxamic acid (SAHA), oxamflatin, suberic bishydroxamic acid (SBHA), m-carboxy-cinnamic acid bishydroxamic acid (CBHA), and pyroxamide. Examples of cyclic peptides include, but are not limited to, trapoxin A, apicidin and FR901228. Examples of benzamides include but are not limited to MS-27-275. Examples of short-chain fatty acids include but are not limited to butyrates (e.g., butyric acid and phenylbutyrate (PB)). Chemical structures for some of these histone deacetylase inhibitors are shown in FIG. 2.

1. Aberrant DNA Methylation of Cancer-Related Genes

In mammalian cells, approximately 3% to 5% of the cytosine residues in genomic DNA are present as 5-methylcytosine. Ehrlich et al (1982) Nucleic Acid Res. 10:2709–2721. This modification of cytosine takes place after DNA replication and is catalyzed by DNA methyltransferase using S-adenosyl-methionine as the methyl donor. Approximately 70% to 80% of 5-methylcytosine residues are found in the CpG sequence. Bird (1986) Nature 321:209–213. This sequence, when found at a high frequency, in the genome, is referred to as CpG islands. Unmethylated CpG islands are associated with housekeeping genes, while the islands of many tissue-specific genes are methylated, except in the tissue where they are expressed. Yevin and Razin (1993) in DNA Methylation: Molecular Biology and Biological Significance. Basel: Birkhauser Verlag, p523–568. This methylation of DNA has been proposed to play an important role in the control of expression of different genes in eukaryotic cells during embryonic development. Consistent with this hypothesis, inhibition of DNA methylation has been found to induce differentiation in mammalian cells. Jones and Taylor (1980) Cell 20:85–93.

Methylation of DNA in the regulatory region of a gene can inhibit transcription of the gene. This may be because 5-methylcytosine protrudes into the major groove of the DNA helix, which interferes with the binding of transcription factors.

The methylated cytosine in DNA, 5-methylcytosine, can undergo spontaneous deamination to form thymine at a rate much higher than the deamination of cytosine to uracil. Shen et al. (1994) Nucleic Acid Res. 22:972–976. If the deamination of 5-methylcytosine is unrepaired, it will result in a C to T transition mutation. For example, many "hot spots" of DNA damages in the human p53 gene are associated with CpG to TpG transition mutations. Denissenko et al. (1997) Proc. Natl. Acad. Sci. USA 94:3893–1898.

Other than p53 gene, many tumor suppressor genes can also be inactivated by aberrant methylation of the CpG islands in their promoter regions. Many tumor-suppressors and other cancer-related genes have been found to hypermethylated in human cancer cells and primary tumors. Examples of genes that participate in suppressing tumor growth and are silenced by aberrant methylation include, but are not limited to, tumor suppressors such as p 15/INK4B (cyclin kinase inhibitor, p16/INK4A (cyclin kinase inhibitor), p73 (p53 homology), ARF/INK4A (regular level p53), Wilms tumor, von Hippel Lindau (VHL), retinoic acid receptor-β(RAR-β), estrogen receptor, androgen receptor, mammary-derived growth inhibitor hypermethylated in cancer (HIC1), and retinoblastoma (Rb); Invasion/metastasis suppressor such as E-cadherin, tissue inhibitor metalloproteinase-2 (TIMP-3), mts-1 and CD44; DNA repair/detoxify carcinogens such as methylguanine methyltransferase, hMLH1 (mismatch DNA repair), glutathione S-transferase, and BRCA-1; Angiogenesis inhibitors such as thrombospondin-1 (TSP-1) and TIMP3; and tumor antigens such as MAGE-1.

In particular, silencing of p16 is frequently associated with aberrant methylation in many different types of cancers. The p16/INK4A tumor suppressor gene codes for a constitutively expressed cyclin-dependent kinase inhibitor, which plays a vital role in the control of cell cycle by the cyclin D-Rb pathway. Hamel and Hanley-Hyde (1997) Cancer Invest. 15:143–152. P16 is located on chromosome 9p, a site that frequently undergoes losss of heterozygosity (LOH) in primary lung tumors. In these cancers, it is postulated that the mechanism responsible for the inactivation of the non-deleted allele is aberrant methylation. Indeed, for lung carcinoma cell lines that did not express p16, 48% showed signs of methylation of this gene. Otterson et al. (1995) Oncogene 11:1211–1216. About 26% of primary non-small cell lung tumors showed methylation of p16. Primary tumors of the breast and colon display 31% and 40% methylation of p16, respectively. Herman et al. (1995) Cancer Res. 55:4525–4530.

Aberrant methylation of retinoic acid receptors are also attributed to development of breast cancer, lung cancer, ovarian cancer, etc. Retinoic acid receptors are nuclear transcription factors that bind to retinoic acid responsive elements (RAREs) in DNA to activate gene expression. In particular, the putative tumor suppressor RAR-β gene is located at chromosome 3p24, a site that shows frequent loss of heterozygosity in breast cancer. Deng et al. (1996) Science 274:2057–2059. Transfection of RAR-β cDNA into some tumor cells induced terminal differentiation and reduced their tumorigenicity in nude mice. Caliaro et al. (1994) Int. J. Cancer 56:743–748; and Houle et al. (1993) Proc. Natl. Acad. Sci. USA 90:985–989. Lack of expression of the RAR-β gene has been reported for breast cancer and other types of cancer. Swisshelm et al. (1994) Cell Growth Differ. 5:133–141; and Crowe (1998) Cancer Res. 58:142–148. This reason for lack of expression of RAR-β gene is attributed to methylation of RAR-β gene. Indeed, methylation of RAR-β was detected in 43% of primary colon carcinomas and in 30% of primary breast carcinoma. Cote et al. (1998) Anti-Cancer Drugs 9:743–750; and Bovenzi et al. (1999) Anticancer Drugs 10:471–476.

Methylation of CpG islands in the 5'-region of the estrogen receptor gene has been found in multiple tumor types. Issa et al. (1994) J. Natl. Cancer Inst. 85:1235–1240. The lack of estrogen receptor expression is a common feature of hormone unresponsive breast cancers, even in the absent of gene mutation. Roodi et al. (1995) J. Natl. Cancer Inst. 87:446–451. About 25% of primary breast tumors that were estrogen receptor-negative displayed aberrant methylation at one site within this gene. Breast carcinoma cell lines that do not express the mRNA for the estrogen receptor displayed increased levels of DNA methyltransferase and extensive methylation of the promoter region for this gene. Ottaviano et al. (1994) 54:2552–2555.

Methylation of human mismatch repair gene (hMLH-1) is also found in various tumors. Mismatch repair is used by the cell to increase the fidelity of DNA replication during cellular proliferation. Lack of this activity can result in mutation rates that are much higher than that observed in normal cells. Modrich and Lahue (1996) Annu. Rev. Biochem. 65:101–133. Methylation of the promoter region of the mismatch repair gene (hMLH-1) was shown to correlate with its lack of expression in primary colon tumors, whereas normal adjacent tissue and colon tumors the expressed this gene did not show signs of its methylation. Kane et al. (1997) Cancer Res. 57:808–811.

The molecular mechanisms by which aberrant methylation of DNA takes place during tumorigenesis are not clear. It is possible that the DNA methyltransferase makes mistakes by methylating CpG islands in the nascent strand of DNA without a complementary methylated CpG in the parental strand. It is also possible that aberrant methylation may be due to the removal of CpG binding proteins that "protect" these sites from being methylated. Whatever the mechanism, the frequency of aberrant methylation is a rare event in normal mammalian cells.

2. Decitabine as an Inhibitor of DNA Methylation

Decitabine, 5-aza-2'-deoxycytidine, is an antagonist of its related natural nucleoside, deoxycytidine. The only structural difference between these two compounds is the presence of a nitrogen at position 5 of the cytosine ring in decitabine as compared to a carbon at this position for deoxycytidine. Two isomeric forms of decitabine can be distinguished. The β-anomer is the active form. The modes of decomposition of decitabine in aqueous solution are (a) conversion of the active b-anomer to the inactive β-anomer (Pompon et al. (1987) J. Chromat. 388:113–122); (b) ring cleavage of the aza-pyrimidine ring to form N-(formylamidino)-N'-β-D-2'-deoxy-(ribofuranosy)-urea (Mojaverian and Repta (1984) J. Pharm. Pharmacol. 36:728–733); and (c) subsequent forming of guanidine compounds (Kissinger and Stemm (1986) J. Chromat. 353:309–318).

Decitabine possesses multiple pharmacological characteristics. At a molecular level, it is capable of specifically inhibiting cell growth at S phase and DNA methylation. At a cellular level, decitabine can induce cell differentiation and exert hematological toxicity. Despite having a short half life in vivo, decitabine has excellent tissue distribution.

The most prominent function of decitabine is its ability to specifically and potently inhibit DNA methylation. As described above for methylation of cytosine in CpG islands as an example, methylation of cytosine to 5-methylcytosine occurs at the level of DNA. Inside the cell, decitabine is first converted into its active form, the phosphorylated 5-aza-deoxycytidine, by deoxycytidine kinase which is primarily synthesized during the S phase of the cell cycle. The affinity of decitabine for the catalytical site of deoxycytidine kinase is similar to the natural substrate, deoxycytidine. Momparler et al. (1985) 30:287–299. After conversion to its triphosphate form by deoxycytidine kinase, decitabine is incorporated into replicating DNA at a rate similar to that of the natural substrate, dCTP. Bouchard and Momparler (1983) Mol. Pharmacol. 24:109–114.

Incorporation of decitabine into the DNA strand has a hypomethylation effect. Each class of differentiated cells has its own distinct methylation pattern. After chromosomal duplication, in order to conserve this pattern of methylation, the 5-methylcytosine on the parental strand serves to direct methylation on the complementary daughter DNA strand. Substistuting the carbon at the 5 position of the cytosine for a nitrogen interferes with this normal process of DNA methylation. The replacement of 5-methylcytosine with decitabine at a specific site of methylation produces an irreversible inactivation of DNA methyltransferase, presumably due to formation of a covalent bond between the enzyme and decitabine. Juttermann et al. (1994) Proc. Natl. Acad. Sci. USA 91:11797–11801. By specifically inhibiting DNA methyltransferase, the enzyme required for methylation, the aberrant methylation of the tumor suppressor genes can be prevented.

According to the present invention, the inventors take advantage of the ability of DNA methylation inhibitors, such as decitabine, reactivate the tumor suppressor genes silenced by aberrant methylation. By reducing methylation, these agents cancer render more effective anti-neoplastic agents whose pharmaceutical activity are adversely affected by methylation in vivo.

3. Histone Deacetylase and Silencing of Genes

The DNA of all chromosomes is packaged into a compact structure with the aid of specialized proteins. The DNA-binding proteins in eucaryotes are divided into tow general classes: the histones and the nonhistone chromosomal proteins. The complex of both classes of protein with the nuclear DNA of eucaryotic cells is known as chromatin. Histones are unique to eucaryotes and the principal structural proteins of eucaryotic chromosomes. They are present in such enormous quantities that their total mass in chromatin is about equal to that of the DNA.

Up till now there are five types of histones identified in chromatin: H1, H2A, H2B, H3, and H4. These five types of histones fall into two main groups: the nucleosomal histones and the H1 histones. The nucleosomal histones (H2A, H2B, H3, and H4) are small proteins (1-2-105 amino acids) responsible for coiling the DNA into nucleosomes. The H1 histones are larger (containing about 220 amino acids). They occur in chromatin in about half the amount of the other types of histones and appear to lie on the outer portion of the nucleosome.

Histones play a crucial part in packing of chromosomal DNA and activation of genes within. Histones pack the very long helix of DNA in each chromosome in an orderly way into a nucleus only a few micro meters in diameters. The role of histones in DNA folding is important in that the manner in which a region of the genome is packaged into chromatin in a particular cell influences the activity of the genes the region contains.

Chromatin structure of transcribed genes is less decondensed than that of the untranscribed or silenced genes. Studies have shown that transcriptionally active chromatin is biochemically distinct from that of the inactive chromatin. The analysis of the chromosomal proteins in the active chromatin suggested the following biophysical and biochemical characteristics: 1) Histone H1 seems to be less tightly bound to at least some active chromatin; 2) the four nucleosomal histones appear to be unusually highly acetylated when compared with the same histones in inactive chromatin; and 3) the nucleosomal histone H2B in active chromatin appears to be less phosphorylated than it is in inactive chromatin. These changes in chromatin features play an important part in uncoiling the chromatin of active genes, helping to make the DNA available as a template for RNA synthesis during transcription of the gene.

In particular, acetylation and deacetylase of histone plays important roles in regulation of gene expression. It has been demonstrated that chromatin fractions enriched in actively transcribed genes are also enriched in highly acetylated core histones, whereas silent genes are associated with nucleosomes with a low level of acetylation. Kouzarides (1999) Curr. Opin Genet Dev. 9:40–48.

Since histones have a very high proportion of positively charged amino acids (lysine and arginine): the positive charge helps the histones bind tightly to DNA which is highly negatively charged, regardless of its nucleotide sequence. Acetylation of histones, particularly in -amino group of lysine, neutralizes the charge of the histones and generate a more open DNA conformation. Such an open conformation of chromatin DNA provides access to transcription factors and the transcription machinery, which in turn promotes expression of the corresponding genes. Conversely, deacetylase of histones restores positive charge to the amino acids and results in tighter binding of histones to the negatively charged phosphate backbone of DNA. Such a condensed chromatin DNA conformation is relatively inaccessible to the transcription machinery and thus the genes in the condensed area are not expressed, i.e. silenced.

4. Inhibitors of Histone Deacetylase

The amount of acetylation on the histones is controlled by the opposing activities of two types of enzymes, histone acetyl transferase (HATs) and histone deacetylases (HDACs). Substrates for these enzymes include e-amino groups of lysine residues located in the amino-terminal tails of the histones H3, H4, H2A, and H2B. These amino acid residues are acetylated by HATs and deacetylated by HDACs. With the removal of the acetyl groups from the histone lysine by HDACs, a positive charge is restored to the lysine residue, thereby condensing the structure of nucleosome and silencing the genes contained within. Thus, to activate these genes silenced by deacetylase of histones, the activity of HADCs should be inhibited. With the inhibition of HDAC, histones are acetylated and the DNA that is tightly wrapped around a deacetylated histone core relaxes. The opening of DNA conformation leads to expression of specific genes.

In addition to deacelation of histones, HDACs may also regulated gene expression by deacetylating transcription factors, such as p53 (a tumor suppressor gene), GATA-1, TFIIE, and TFIIF. Gu and Roeder (1997) Cell 90:595–606 (p53); and Boyes et al. (1998) Nature 396:594–598 (GATA-1). HDACs also participate in cell cycle regulation, for example, by transcription repression which is mediated by RB tumor suppressor proteins recruiting HDACs. Brehm et al. (1998) Nature 391:597–601. Thus, inhibition of HDACs should activate expression of tumor suppressor genes such as p53 and RB and as a result promote cell growth arrest, differentiation and apoptosis induced by these genes.

Inhibitors of HDACs include, but are not limited to, the following structural classes: 1) hydroxamic acids, 2) cyclic peptides, 3) benzamides, and 4) short-chain fatty acids. Chemical structures for some of these HDAC inhibitors are shown in FIG. 2.

Examples of hydroxamic acids and hydroxamic acid derivatives, but are not limited to, trichostatin A (TSA), suberoylanilide hydroxamic acid (SAHA), oxamflatin, suberic bishydroxamic acid (SBHA), m-carboxy-cinnamic acid bishydroxamic acid (CBHA), and pyroxamide. TSA was isolated as an antifungi antibiotic (Tsuji et al (1976) J. Antibiot (Tokyo) 29:1–6) and found to be a potent inhibitor of mammalian HDAC (Yoshida et al. (1990) J. Biol. Chem. 265:17174–17179). The finding that TSA-resistant cell lines have an altered HDAC evidences that this enzyme is an important target for TSA. Other hydroxamic acid-based HDAC inhibitors, SAHA, SBHA, and CBHA are synthetic compounds that are able to inhibit HDAC at micromolar concentration or lower in vitro or in vivo. Glick et al. (1999) Cancer Res. 59:4392–4399. These hydroxamic acid-based HDAC inhibitors all possess an essential structural feature: a polar hydroxamic terminal linked through a hydrophobic methylene spacer (e.g. 6 carbon at length) to another polar site which is attached to a terminal hydrophobic moiety (e.g., benzene ring). Compounds developed having such essential features also fall within the scope of the hydroxamic acids that may be used as HDAC inhibitors.

Cyclic peptides used as HDAC inhibitors are mainly cyclic tetrapeptides. Examples of cyclic peptides include, but are not limited to, trapoxin A, apicidin and FR901228. Trapoxin A is a cyclic tetrapeptide that contains a 2-amino-8-oxo-9,10-epoxy-decanoyl (AOE) moiety. Kijima et al. (1993) J. Biol. Chem. 268:22429–22435. Apicidin is a fungal metabolite that exhibits potent, broad-spectrum antiprotozoal activitity and inhibits HDAC activity at nanomolar concentrations. Darkin-Rattray et al. (1996) Proc. Natl. Acad. Sci. USA. 93; 13143–13147. FR901228 is a depsipeptide that is isolated from *Chromobacterium violaceum*, and has been shown to inhibit HDAC activity at micromolar concentrations.

Examples of benzamides include but are not limited to MS-27–275. Saito et al. (1990) Proc. Natl. Acad. Sci. USA. 96:4592–4597. Examples of short-chain fatty acids include but are not limited to butyrates (e.g., butyric acid, arginine butyrate and phenylbutyrate (PB)). Newmark et al. (1994) Cancer Lett. 78:1–5; and Carducci et al. (1997) Anticancer Res. 17:3972–3973. In addition, depudecin which has been shown to inhibit HDAC at micromolar concentrations (Kwon et al. (1998) Proc. Natl. Acad. Sci. USA. 95:3356–3361) also falls within the scope of histone deacetylase inhibitor of the present invention.

5. Anti-Neoplastic Agents that May be Used in Conjunction with the Combination of the DNA Methylation Inhibitor and the Histone Deacetylase Inhibitor A wide variety of anti-neoplastic agents may be used in conjunction with the combination of the DNA methylation inhibitor and the histone deacetylase inhibitor for treating various diseases associated with abnormal cell proliferation such as cancer. The particular anti-neoplastic agent(s) used in conjunction with the DNA methylation inhibitor and the histone deacetylase inhibitor may depend on the particular type of cancer to be treated.

The antineoplastic agent may be an antibiotic agent. Antibiotic agents are a group of anticancer drugs that are produced in a manner similar to antibiotics by a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and form an activated complex, which then binds to bases of DNA, causing strand scissions and cell death. Such a combination therapy may have therapeutic synergistic effects on cancer and reduce sides affects associated with these chemotherapeutic agents.

The antineoplastic agent may be an antimetabolic agent. Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Such a combination therapy may have therapeutic synergistic effects on cancer and reduce sides affects associated with these chemotherapeutic agents.

The antineoplastic agent may also be a plant-derived agent. Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), water soluble or insoluble camptothecin (e.g. 20(S)-camptothecin, 9-nitro-camptothecin, 9-nitro-camptothecin, and topotecan), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Camptothecin is believed to be a potent inhibitor of the nuclear enzyme DNA topoisomerase I (topo-I), which is responsible for "relaxation" of supercoiled double-stranded DNA by creating single-stranded breaks through which another DNA strand can pass during transcription. Topo-I reseals the break allowing DNA replication to occur. Inhibition of topo-I leads to the formation of stable DNA-topoisomerase complexes, with eventual formation of irreversible double-stranded DNA breaks, leading to apoptosis and/or other forms of cell death. Podophyllotoxins such as etoposide are believed to interfere with DNA synthesis by interacting with topoisomerase II, leading to DNA strand scission. Such a combination therapy may have therapeutic synergistic effects on cancer and reduce sides affects associated with these chemotherapeutic agents.

The antineoplastic agent may be a biologic agent. Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a DNA methylation inhibitor, a histone deacetylase inhibitor and the biologic agent may have therapeutic synergistic effects on cancer, enhance the patient's immune responses to tumorigenic signals, and reduce potential sides affects associated with this biologic agent.

Cytokines possess profound inmmunomodulatory activity. Some cytokines such as interleukin-2 (IL-2, aldesleukin) and interferon-α (IFN-α) demonstrate antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with a DNA methylation inhibitor include, but are not limited to, interleukin 2 (IL-2), and interleukin 4 (IL-4), interleukin 12 (IL-12).

Interferon-α includes more than 23 related subtypes with overlapping activities, all of the IFN-α subtypes within the scope of the present invention. IFN-has demonstrated activity against many solid and hematologic malignancies, the later appearing to be particularly sensitive. Examples of interferons that may be used in conjunction with a DNA methylation inhibitor include, but are not limited to, interferon-α, interferon-β (fibroblast interferon) and interferon-γ (fibroblast interferon).

Other cytokines that may be used in conjunction with a DNA methylation inhibitor include those cytokines that exert profound effects on hematopoiesis and immune functions. Examples of such cytokines include, but are not limited to erythropoietin (epoietin-α), granulocyte-CSF (filgrastin), and granulocyte, macrophage-CSF (sargramostim). These cytokines may be used in conjunction with a DNA methylation inhibitor to reduce chemotherapy-induced myelopoietic toxicity.

Immuno-modulating agents other than cytokines may also be used in conjunction with a DNA methylation inhibitor to inhibit abnormal cell growth. Examples of such immuno-modulating agents include, but are not limited to bacillus Calmette-Guerin, levamisole, and octreotide, a long-acting octapeptide that mimics the effects of the naturally occuring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including a DNA methylation inhibitor and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and maligant $CD20^+$ pre-B and mature B cells. RITUXAN® is used as single agent for the treatment of patients with relapsed or refractory low-grade or follicular, CD20+, B cell non-Hodgkin's lymphoma. Combination therapy including a DNA methylation inhibitor and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutions in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

6. Indications for Treatment

Preferable indications that may be treated using the compositions of the present invention include those involving undesirable or uncontrolled cell proliferation. Such indications include benign tumors, various types of cancers such as primary tumors and tumor metastasis, hematologic disorders (e.g. leukemia, myelodysplastic syndrome and sickle cell anemia), restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include leukemia, breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chormosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrom), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanim of various angiogenic factors, including elements of the inflammatory response, such as leukocytes, platelets, cytokines, and eicosanoids, or unidentified plasma constituents have yet to be revealed.

In another embodiment of the present invention, a method is provided for treating diseases associated with undesired or abnormal angiogenesis. The method comprises administering to a patient suffering from undesired or abnormal angiogenesis a composition comprising a combination of a DNA methylation inhibitor and a histone deacetylase inhibitor alone or in conjunction with an anti-angiogenesis agent.

The particular dosage of these agents required to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the composition of the present invention may be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment of the present invention, a method is provided for treating chronic inflammatory diseases associated with abnormal angiogenesis. The method comprises administering to a patient suffering from a chronic inflammatory disease associated with abnormal angiogenesis a composition comprising a DNA methylation inhibitor and a histone deacetylase inhibitor. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the composition of the present invention may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rhematoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the composition of the present invention should inhibit the formation of the sprouts and prevent the formation of granulomas. The inflammatory bowel diseases also exhibit extra intestinal manifectations, such as skin lesions. Such lesions are characterized by inflammation and angiogenesis and can occur at many sites other the gastrointestinal tract. Inhibition of angiogenesis by the composition of the present invention should reduce the influx of inflammatory cells and prevent the lesion formation.

Sarcoidois, another chronic inflammatory disease, is characterized as a multisystem granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the composition of the present invention to inhibit angionesis, such granulomas formation can be inhibited. Psoriasis, also a chronic and recurrent inflammatory disease, is characterized by papules and plaques of various sizes. Treatment using the composition of the present invention should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the composition of the present invention alone or in conjunction with other anti-RA agents should prevent the formation of new blood vessels necessary to maintain the chronic inflammation and provide the RA patient relief from the symptoms.

7. Routes of Administration and Dosing Regimen

A wide variety of delivery methods and formulations for different delivery methods may be used in the combination therapies of the present invention.

The inventive combination of therapeutic agents may be administered as compositions that comprise the inventive combination of therapeutic agents. Such compositions may include, in addition to the inventive combination of therapeutic agents, conventional pharmaceutical excipients, and other conventional, pharmaceutically inactive agents. Additionally, the compositions may include active agents in addition to the inventive combination of therapeutic agents.

These additional active agents may include additional compounds according to the invention, or one or more other pharmaceutically active agents. In preferable embodiments, the inventive compositions will contain the active agents, including the inventive combination of therapeutic agents, in an amount effective to treat an indication of interest.

The inventive combination of therapeutic agents and/or compositions may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The inventive combination of therapeutic agents and compositions may be administered by a variety of routes, and may be administered or coadministered in any conventional dosage form. Coadministration in the context of this invention is defined to mean the administration of more than one therapeutic in the course of a coordinated treatment to achieve an improved clinical outcome. Such coadministration may also be coextensive, that is, occurring during overlapping periods of time. For example, the DNA methylation inhibitor may be administered to a patient before, concomitantly, or after the histone deacetylase inhibitor is administered. In a preferred embodiment, the patient may be pretreated with the DNA methylation inhibitor (e.g., decitabine) and then treated with the histone deacetylase inhibitor (e.g., depsipeptide).

Amounts of the inventive combination of therapeutic agents can vary, according to determinations made by one of skill, but preferably are in amounts effective to create a cytotoxic or cytostatic effect at the desired site. Preferably, these total amounts are less than the total amount adding the maximum tolerated dose for each of the DNA methylation inhibitor and the histone deacetylase inhibitor, and more preferably less than the total amount added for individual administration of each of these inhibitors.

For the slow-release dosage form, appropriate release times can vary, but preferably should last from about 1 hour to about 6 months, most preferably from about 1 week to about 4 weeks. Formulations including the inventive combination of therapeutic agents and/or composition can vary, as determinable by one of skill, according to the particular situation, and as generally taught herein.

Decitabine may be supplied as sterile powder for injection, together with buffering salt such as potassium dihydrogen and pH modifier such as sodium hydroxide. This formulation is preferably stored at 2–8° C., which should keep the drug stable for at least 2 years. This powder formulation may be reconstituted with 10 ml of sterile water for injection. This solution may be further diluted with infusion fluid known in the art, such as 0.9% sodium chloride injection, 5% dextrose injection and lactated ringer's injection. It is preferred that the reconstituted and diluted solutions be used within 4–6 hours for delivery of maximum potency.

In a preferred embodiment, decitabine is administrated to a patient by injection, such as bolus i.v. injection, continuous i.v. infusion and i.v. infusion over 1 hour. For example, decitabine may administered into the patient via an 1–24 hour i.v. infusion per day for 3–5 days per treatment cycle at a dose preferably ranging from 1–100 mg/m$^2$, more preferably ranging from 2–50 mg/m$^2$, and most preferably from 5–20 mg/m$^2$. The preferred dosage below 50 mg/m$^2$ for decitabine is considered to be much lower than that used in conventional chemotherapy for cancer. By using such a low dose of decitabine, transcriptional activity of genes silenced in the cancer cells can be activated to trigger downstream signal transduction for cell growth arrest, differentiation and apoptosis which eventually results death of these cancer cells. This low dosage, however, should have less systemic cytotoxic effect on normal cells, and thus have less side effects on the patient being treated.

For the histone deacetylase inhibitor, the dosage form depends on the type of compound used as the inhibitor. For example, depsipeptide may be formulated for i.v. infusion.

In an embodiment, depsipeptide is administered to a patient by continuous i.v. infusion for at least 4 hours per day for a week at a dose preferably ranging from 2–100 mg/m$^2$, more preferably ranging from 5–50 mg/m$^2$, and most preferably from 5–15 mg/m$^2$. The treatment cycle may be 1 or 2 weeks per month.

In another embodiment, phenylbutyrate (PB) is administered to a patient by continuous i.v. infusion at a dose preferably ranging from 100–2000 mg/m$^2$, more preferably ranging from 250–1000 mg/m$^2$, and most preferably from 500–800 mg/m$^2$.

In another embodiment, arginine butyrate is administered to a patient by continuous i.v. infusion at a dose preferably ranging from 100–2000 mg/m$^2$, more preferably ranging from 250–1000 mg/m$^2$, and most preferably from 500–800 mg/m$^2$. For example, arginine butyrate may be administered at a dose between 250–1000 mg/m$^2$ as a 6–12 hour iv infusion for 4 days every 2 weeks.

In preferred embodiment, depsipeptide is administered after administration of decitabine to the patient. This clinical regimen is designed to enhance efficacy of the combination therapy by sensitizing the cancers to apoptosis signals through inhibition of methylation and then triggering cell death by depsipeptide-induced apoptosis mechanism.

Also according to the present invention, after the treatment with the DNA methylation inhibitor and histone deacetylase inhibitor, the patient may be further treated with various anticancer agents described above. Owing to the sensitizing effects of the combination therapy on the cells to apoptosis, the dosage of anticancer agents used for the treatment may be lower than that used in a convention cancer treatment regimen. Thus, a better clinical outcome may be achieved by using the compositions and methods of the present invention.

The inventive combination of therapeutic agents may be used in the form of kits. The arrangement and construction of such kits is conventionally known to one of skill in the art. Such kits may include containers for containing the inventive combination of therapeutic agents and/or compositions, and/or other apparatus for administering the inventive combination of therapeutic agents and/or compositions.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A method for treating a patient having a cancer with a combination therapy, comprising:
   administering to said patient a therapeutically effective amount of a DNA methylation inhibitor that is 5-azacytidine or decitabine at a dose ranging from 1 to 50 mg/M² per day, in combination with a therapeutically effective amount of a histone deacetylase inhibitor selected from the group consisting of trichostatin A, suberoylanilide hydroxamic acid, oxamflatin, suberic bishydroxamic acid, m-carboxy-cinnamic acid bishydroxamic acid, pyroxamide, trapoxin A, apicidin, depsipeptide, N-(2-aminophenyl)-4-[N-(pyridin-3-ylmethoxycarbonyl)aminomethyl]benzamide, butyric acid, phenylbutyrate and arginine butyrate.

2. The method according to claim 1, wherein the cancer is selected from the group consisting of breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstone tumor, islet cell tumor, primary brain tumor, acute and chronic lymphocytic and granulocytic tumors, hairy-cell tumor, adenoma, hyperplasia, medullary carcinoma, pheochromocytoma, mucosal neuromas, interstinal ganglioneuromas hyperplastic comeal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic sarcoma, malignant hypercalcemia, renal cell tumor, polycythemia vera, adenocarcinoma, glioblastoma multiforma, acute myeloid leukemia, acute promyelocytic leukemia, acute lymphoblastic leukemia, chronic myelogenous leukemia, myelodysplastic syndrome, lymphomas, malignant melanomas, and epidermoid carcinomas.

3. The method of claim 1, wherein administering to the patient includes administering the DNA methylation inhibitor and the histone deacetylase inhibitor orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, or intrathecally.

4. The method of claim 1, wherein the DNA methylation inhibitor is decitabine and is administered intravenously or subcutaneously.

5. The method of claim 4, wherein decitabine is administered to the patient via an intravenous infusion per day at a dose ranging from 2 to 50 mg/m².

6. The method of claim 4, wherein decitabine is administered to the patient via an intravenous infusion per day at a dose ranging from 5 to 20 mg/m².

7. The method of claim 4, wherein decitabine is administered to the patient via an intravenous infusion at a dose ranging from 1 to 50 mg/m² per day for at least 3 days per treatment cycle.

8. The method of claim 1, wherein the histone deacetylase inhibitor is depsipeptide and is administered intravenously.

9. The method of claim 8, wherein depsipeptide is administered to the patient by continuous intravenous infusion for at least 4 hours per day for a week at a dose ranging from 2 to 100 mg/m².

10. The method of claim 8, wherein depsipeptide is administered to the patient by continuous intravenous infusion for at least 4 hours per day for a week at a dose ranging from 5 to 50 mg/m².

11. The method of claim 8, wherein depsipeptide is administered to the patient by continuous intravenous infusion for at least 4 hours per day for a week at a dose ranging from 5 to 15 mg/m².

12. The method of claim 1, wherein the histone deacetylase inhibitor is phenylbutyrate and is administered intravenously.

13. The method of claim 12, wherein phenylbutyrate is administered to the patient by continuous intravenous infusion for at least 2 to 3 weeks at a dose ranging from 100–2000 mg/m².

14. The method of claim 12, wherein phenylbutyrate is administered to the patient by continuous intravenous infusion for at least 2 to 3 weeks at a dose ranging from 250–1000 mg/m².

15. The method of claim 12, wherein phenylbutyrate is administered to the patient by continuous intravenous infusion for at least 2 to 3 weeks at a dose ranging from 500–800 mg/m².

16. The method of claim 1, wherein the DNA methylation inhibitor is administered prior to the administration of the histone deacetylase inhibitor.

17. The method of claim 1, further comprising administering an antibiotic agent.

18. The method of claim 17, wherein the antibiotic agent is selected from the group consisting of doxorubicin, daunorubicin, epirubicin, idarubicin and anthracenedione, mitomycin C, bleomycin, dactinomycin, and plicatomycin.

* * * * *